United States Patent
George

(10) Patent No.: US 11,246,578 B2
(45) Date of Patent: Feb. 15, 2022

(54) TISSUE COLLECTION BAGS WITH INNER SURFACE POUCHES

(71) Applicant: Covidien LP, Mansfield, MA (US)

(72) Inventor: Sabastian Koduthully George, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 30 days.

(21) Appl. No.: 16/829,923

(22) Filed: Mar. 25, 2020

(65) Prior Publication Data

US 2020/0360003 A1   Nov. 19, 2020

Related U.S. Application Data

(60) Provisional application No. 62/847,971, filed on May 15, 2019.

(51) Int. Cl.
*A61B 17/00* (2006.01)

(52) U.S. Cl.
CPC .......... *A61B 17/00234* (2013.01); *A61B 2017/00287* (2013.01); *A61B 2017/00871* (2013.01); *A61B 2017/00907* (2013.01)

(58) Field of Classification Search
CPC .......... A61B 17/00234; A61B 17/221; A61B 17/3423; A61B 2017/00287; A61B 2017/00557; A61B 2017/00592; A61B 2017/00871; A61B 2017/00907; A61B 5/15003; A61B 5/150045; A61B 5/150251; A61B 5/153
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |

(Continued)

FOREIGN PATENT DOCUMENTS

| | | |
|---|---|---|
| DE | 25796 C | 1/1884 |
| DE | 3542667 A1 | 6/1986 |

(Continued)

OTHER PUBLICATIONS

European Search Report EP 12191639.9 dated Feb. 20, 2013.

(Continued)

*Primary Examiner* — Mohamed G Gabr
(74) *Attorney, Agent, or Firm* — Carter, DeLuca & Farrell LLP

(57) ABSTRACT

A collection bag for specimen retrieval includes an outer surface and an inner surface. The inner surface includes pouches that prevent fluid from migrating out of the collection bag. The collection bag can be selectively coupled to an end effector of a specimen retrieval device. The pouches may be arranged in one or more rows about the inner surface of the collection bag. The pouches can be inverted so that pockets of the pouches open toward a bottom end portion of the collection bag.

16 Claims, 5 Drawing Sheets

(56) References Cited

U.S. PATENT DOCUMENTS

| | | | |
|---|---|---|---|
| 4,852,586 | A | 8/1989 | Haines |
| 4,927,427 | A | 5/1990 | Kriauciunas et al. |
| 4,977,903 | A | 12/1990 | Haines |
| 4,991,593 | A | 2/1991 | LeVahn |
| 4,997,435 | A | 3/1991 | Demeter |
| 5,037,379 | A | 8/1991 | Clayman et al. |
| 5,074,867 | A | 12/1991 | Wilk |
| 5,084,054 | A | 1/1992 | Bencini et al. |
| 5,143,082 | A | 9/1992 | Kindberg et al. |
| 5,147,371 | A | 9/1992 | Washington et al. |
| 5,176,687 | A | 1/1993 | Hasson et al. |
| 5,190,542 | A | 3/1993 | Nakao et al. |
| 5,190,555 | A | 3/1993 | Wetter et al. |
| 5,190,561 | A | 3/1993 | Graber |
| 5,192,284 | A | 3/1993 | Pleatman |
| 5,192,286 | A | 3/1993 | Phan et al. |
| 5,201,740 | A | 4/1993 | Nakao et al. |
| 5,215,521 | A | 6/1993 | Cochran et al. |
| 5,224,930 | A | 7/1993 | Spaeth et al. |
| 5,234,439 | A | 8/1993 | Wilk et al. |
| 5,279,539 | A | 1/1994 | Bohan et al. |
| 5,312,416 | A | 5/1994 | Spaeth et al. |
| 5,320,627 | A | 6/1994 | Sorensen et al. |
| 5,330,483 | A | 7/1994 | Heaven et al. |
| 5,336,227 | A | 8/1994 | Nakao et al. |
| 5,337,754 | A | 8/1994 | Heaven et al. |
| 5,341,815 | A | 8/1994 | Cofone et al. |
| 5,352,184 | A | 10/1994 | Goldberg et al. |
| 5,354,303 | A | 10/1994 | Spaeth et al. |
| 5,360,648 | A | 11/1994 | Falla et al. |
| 5,368,545 | A | 11/1994 | Schaller et al. |
| 5,368,597 | A | 11/1994 | Pagedas |
| 5,370,647 | A | 12/1994 | Graber et al. |
| 5,443,472 | A | 8/1995 | Li |
| 5,465,731 | A | 11/1995 | Bell et al. |
| 5,480,404 | A | 1/1996 | Kammerer et al. |
| 5,486,182 | A | 1/1996 | Nakao et al. |
| 5,486,183 | A | 1/1996 | Middleman et al. |
| 5,499,988 | A | 3/1996 | Espiner et al. |
| 5,524,633 | A | 6/1996 | Heaven et al. |
| 5,535,759 | A | 7/1996 | Wilk |
| 5,611,803 | A | 3/1997 | Heaven et al. |
| 5,618,296 | A | 4/1997 | Sorensen et al. |
| 5,630,822 | A | 5/1997 | Hermann et al. |
| 5,642,282 | A | 6/1997 | Sonehara |
| 5,643,282 | A | 7/1997 | Kieturakis |
| 5,643,283 | A | 7/1997 | Younker |
| 5,645,083 | A | 7/1997 | Essig et al. |
| 5,647,372 | A | 7/1997 | Tovey et al. |
| 5,649,902 | A | 7/1997 | Yoon |
| 5,658,296 | A | 8/1997 | Bates et al. |
| 5,679,423 | A | 10/1997 | Shah |
| 5,681,324 | A | 10/1997 | Kammerer et al. |
| 5,720,754 | A | 2/1998 | Middleman et al. |
| 5,735,289 | A | 4/1998 | Pfeffer et al. |
| 5,741,271 | A | 4/1998 | Nakao et al. |
| 5,755,724 | A | 5/1998 | Yoon |
| 5,759,187 | A | 6/1998 | Nakao et al. |
| 5,769,794 | A | 6/1998 | Conlan et al. |
| 5,782,840 | A | 7/1998 | Nakao |
| 5,785,677 | A | 7/1998 | Auweiler |
| 5,788,709 | A | 8/1998 | Riek et al. |
| 5,792,145 | A | 8/1998 | Bates et al. |
| 5,814,044 | A | 9/1998 | Hooven |
| 5,829,440 | A | 11/1998 | Broad, Jr. |
| 5,836,953 | A | 11/1998 | Yoon |
| 5,853,374 | A | 12/1998 | Hart et al. |
| 5,895,392 | A | 4/1999 | Riek et al. |
| 5,904,690 | A | 5/1999 | Middleman et al. |
| 5,906,621 | A | 5/1999 | Secrest et al. |
| 5,908,429 | A | 6/1999 | Yoon |
| 5,957,884 | A | 9/1999 | Hooven |
| 5,971,995 | A | 10/1999 | Rousseau |
| 5,980,544 | A | 11/1999 | Vaitekunas |
| 5,997,547 | A | 12/1999 | Nakao et al. |
| 6,004,330 | A | 12/1999 | Middleman et al. |
| 6,007,512 | A | 12/1999 | Hooven |
| 6,007,546 | A | 12/1999 | Snow et al. |
| 6,019,770 | A | 2/2000 | Christoudias |
| 6,036,681 | A | 3/2000 | Hooven |
| 6,059,793 | A | 5/2000 | Pagedas |
| 6,123,701 | A | 9/2000 | Nezhat |
| 6,152,932 | A | 11/2000 | Ternstrom |
| 6,156,055 | A | 12/2000 | Ravenscroft |
| 6,162,235 | A | 12/2000 | Vaitekunas |
| 6,165,121 | A | 12/2000 | Alferness |
| 6,168,603 | B1 | 1/2001 | Leslie et al. |
| 6,206,889 | B1 | 3/2001 | Bennardo |
| 6,228,095 | B1 | 5/2001 | Dennis |
| 6,258,102 | B1 | 7/2001 | Pagedas |
| 6,264,663 | B1 | 7/2001 | Cano |
| 6,270,505 | B1 | 8/2001 | Yoshida et al. |
| 6,277,083 | B1 | 8/2001 | Eggers et al. |
| 6,280,450 | B1 | 8/2001 | McGuckin, Jr. |
| 6,344,026 | B1 | 2/2002 | Burbank et al. |
| 6,348,056 | B1 | 2/2002 | Bates et al. |
| 6,350,266 | B1 | 2/2002 | White et al. |
| 6,350,267 | B1 | 2/2002 | Stefanchik |
| 6,368,328 | B1 | 4/2002 | Chu et al. |
| 6,383,195 | B1 | 5/2002 | Richard |
| 6,383,196 | B1 | 5/2002 | Leslie et al. |
| 6,383,197 | B1 | 5/2002 | Conlon et al. |
| 6,387,102 | B2 | 5/2002 | Pagedas |
| 6,406,440 | B1 | 6/2002 | Stefanchik |
| 6,409,733 | B1 | 6/2002 | Conlon et al. |
| 6,419,639 | B2 | 7/2002 | Walther et al. |
| 6,447,523 | B1 | 9/2002 | Middleman et al. |
| 6,471,659 | B2 | 10/2002 | Eggers et al. |
| 6,506,166 | B1 | 1/2003 | Hendler et al. |
| 6,508,773 | B2 | 1/2003 | Burbank et al. |
| 6,537,273 | B1 | 3/2003 | Sosiak et al. |
| 6,547,310 | B2 | 4/2003 | Myers |
| 6,589,252 | B2 | 7/2003 | McGuckin, Jr. |
| 6,716,499 | B1 | 4/2004 | Vadhar |
| 6,752,811 | B2 | 6/2004 | Chu et al. |
| 6,755,779 | B2 | 6/2004 | Vanden Hoek et al. |
| 6,780,193 | B2 | 8/2004 | Leslie et al. |
| 6,805,699 | B2 | 10/2004 | Shimm |
| 6,840,948 | B2 | 1/2005 | Albrecht et al. |
| 6,872,211 | B2 | 3/2005 | White et al. |
| 6,887,255 | B2 | 5/2005 | Shimm |
| 6,958,069 | B2 | 10/2005 | Shipp et al. |
| 6,971,988 | B2 | 12/2005 | Orban, III |
| 6,994,696 | B2 | 2/2006 | Suga |
| 7,014,648 | B2 | 3/2006 | Ambrisco et al. |
| 7,018,373 | B2 | 3/2006 | Suzuki |
| 7,052,454 | B2 | 5/2006 | Taylor |
| 7,052,501 | B2 | 5/2006 | McGuckin, Jr. |
| 7,090,637 | B2 | 8/2006 | Danitz et al. |
| 7,115,125 | B2 | 10/2006 | Nakao et al. |
| 7,270,663 | B2 | 9/2007 | Nakao |
| 7,273,488 | B2 | 9/2007 | Nakamura et al. |
| 7,410,491 | B2 | 8/2008 | Hopkins et al. |
| 7,547,310 | B2 | 6/2009 | Whitfield |
| 7,618,437 | B2 | 11/2009 | Nakao |
| 7,670,346 | B2 | 3/2010 | Whitfield |
| 7,722,626 | B2 | 5/2010 | Middleman et al. |
| 7,762,959 | B2 | 7/2010 | Bilsbury |
| 7,785,251 | B2 | 8/2010 | Wilk |
| 7,819,121 | B2 | 10/2010 | Amer |
| 7,837,612 | B2 | 11/2010 | Gill et al. |
| RE42,050 | E | 1/2011 | Richard |
| 7,892,242 | B2 | 2/2011 | Goldstein |
| 8,016,771 | B2 | 9/2011 | Orban, III |
| 8,057,485 | B2 | 11/2011 | Hollis et al. |
| 8,075,567 | B2 | 12/2011 | Taylor et al. |
| 8,097,001 | B2 | 1/2012 | Nakao |
| 8,152,820 | B2 | 4/2012 | Mohamed et al. |
| 8,172,772 | B2 | 5/2012 | Zwolinski et al. |
| 8,206,401 | B2 | 6/2012 | Nakao |
| 8,337,510 | B2 | 12/2012 | Rieber et al. |
| 8,343,031 | B2 | 1/2013 | Gertner |
| 8,348,827 | B2 | 1/2013 | Zwolinski |
| 8,388,630 | B2 | 3/2013 | Teague et al. |

(56) References Cited

U.S. PATENT DOCUMENTS

| | | |
|---|---|---|
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0256425 A1 | 11/2005 | Prusiner |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2010/0318045 A1* | 12/2010 | Taylor ............ A61B 17/00234 604/317 |
| 2011/0087235 A1 | 4/2011 | Taylor et al. |
| 2011/0184311 A1 | 7/2011 | Parihar et al. |
| 2011/0184434 A1* | 7/2011 | Parihar ............ A61B 17/00234 606/114 |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0249919 A1 | 10/2011 | Shepard |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0158010 A1* | 6/2012 | Menn ............ A61B 17/00234 606/114 |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1* | 12/2013 | Hathaway ........ A61B 17/00234 606/114 |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0311964 A1 | 11/2017 | Desai et al. |
| 2017/0325798 A1 | 11/2017 | Prior |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| DE | 10327106 A1 | 12/2004 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2583629 A2 | 4/2013 |
| ES | 2379920 A1 | 5/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0078545 A1 | 12/2000 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2011090866 A2 | 7/2011 |
| WO | 2013075103 A1 | 5/2013 |
| WO | 2014134285 A1 | 9/2014 |
| WO | 2015134888 A1 | 9/2015 |

(56) References Cited

FOREIGN PATENT DOCUMENTS

| WO | 2015164591 A1 | 10/2015 |
| WO | 2017189442 A1 | 11/2017 |
| WO | 2018148744 A1 | 8/2018 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
Extended European Search Report issued in corresponding Appl. No. EP 19170619.1dated Sep. 19, 2019 (8 pages).
Extended European Search Report issued in Appl. No. 19174966.2 dated Oct. 30, 2019 (10 pages).
Extended European Search Report issued in Appl. No. EP 19197987.1 dated Jan. 8, 2020 (10 pages).

* cited by examiner

TISSUE COLLECTION BAGS WITH INNER SURFACE POUCHES

CROSS-REFERENCE TO RELATED APPLICATION

The present application claims the benefit of and priority to U.S. Provisional Patent Application Ser. No. 62/847,971, filed on May 15, 2019, the entire content of which is incorporated herein by reference.

TECHNICAL FIELD

This disclosure relates to surgical devices, and more particularly, to collection bags for specimen retrieval devices.

BACKGROUND

Specimen retrieval devices are commonly used during surgical procedures to collect and remove tissue specimens from a patient. Typically, during a surgical procedure in which tissue is transected, e.g., a hysterectomy procedure, a specimen retrieval device including a tissue collection bag is positioned to receive the tissue specimen once the tissue is transected. In some procedures, a grasper may be used to transfer the transected tissue specimen into the bag. Alternately, the bag may be positioned in relation to the tissue specimen to allow the tissue specimen to fall into the bag.

SUMMARY

In aspects of the disclosure, a specimen retrieval device includes an elongated shaft and an end effector supported on the elongated shaft. The end effector supports a collection bag. The collection bag includes an inner surface and an outer surface. The inner surface of the collection bag includes a plurality of pouches.

In some embodiments, the pouches may define a pocket configured to prevent fluid from migrating out of the collection bag.

In some embodiments, the pouches are inverted so that the pockets thereof open toward a bottom of the collection bag.

In various embodiments, the pouches may have an arcuate configuration.

In embodiments, the pouches may be arranged in a plurality of rows. At least some of the plurality of rows may be arranged such that pouches in adjacent rows are offset from one another.

In some embodiments, each pouch of the plurality of pouches may be offset from adjacent pouches of the plurality of pouches.

In some embodiments, the specimen retrieval device further includes a pull string assembly that is actuatable to close the collection bag.

In various embodiments, the collection bag may be made at least partially of a polymeric material. The collection bag may be transparent.

According to yet another aspect of this disclosure, a collection bag for a specimen retrieval device includes an outer surface, an inner surface, a bottom end portion, and a top end portion including a plurality of pouches extending from the inner surface.

According to still another aspect of this disclosure, a collection bag for retrieving a tissue specimen includes a closed bottom end portion, an open top end portion that is selectively closable, an outer surface, and an inner surface including a plurality of inverted pouches that open towards the closed bottom end portion.

The details of one or more aspects of the disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
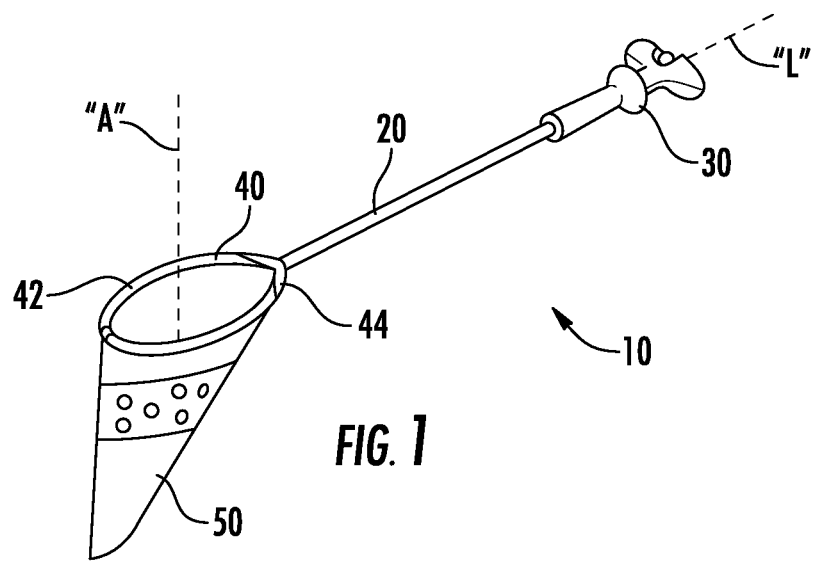
FIG. 1 is a perspective view of one embodiment of a specimen retrieval device in accordance with the principles of this disclosure.

Embodiments of the disclosed specimen retrieval devices are described in detail with reference to the drawings, in which like reference numerals designate identical or corresponding elements in each of the several views. As commonly known, the term "clinician" refers to a doctor (e.g., a surgeon), a nurse, or any other care provider and may include support personnel. Additionally, the term "proximal" refers to the portion of structure that is closer to the clinician and the term "distal" refers to the portion of structure that is farther from the clinician. In the following description, well-known functions or constructions are not described in detail to avoid obscuring this disclosure in unnecessary detail.

In general, this disclosure describes a specimen retrieval device configured to collect tissue specimens and retain associated tissue and fluid, such as blood, collected with a tissue specimen, within a collection bag of the specimen retrieval device.

With reference to FIG. 1, a specimen retrieval device 10 defines a longitudinal axis "L" and includes an elongated shaft assembly 20. Elongated shaft assembly 20 has a proximal end portion that supports a handle assembly 30 and a distal end portion that supports an end effector 40. End effector 40 includes a first arm 42 and a second arm 44 that removably support a collection bag 50.

Figure 2:
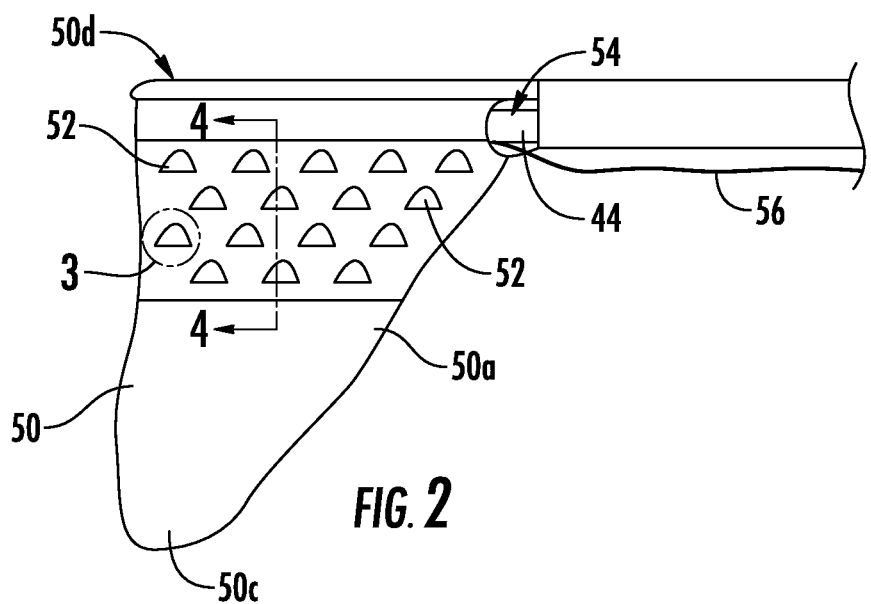
FIG. 2 is a side view of a distal portion of the specimen retrieval device of FIG. 1.
Figure 3:
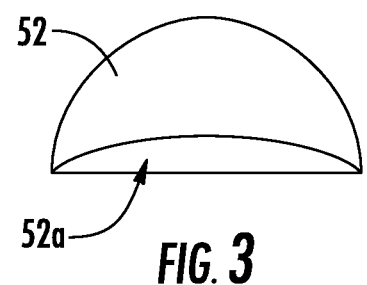
FIG. 3 is an enlarged view of the indicated area of detail shown in FIG. 2.
Figure 4:
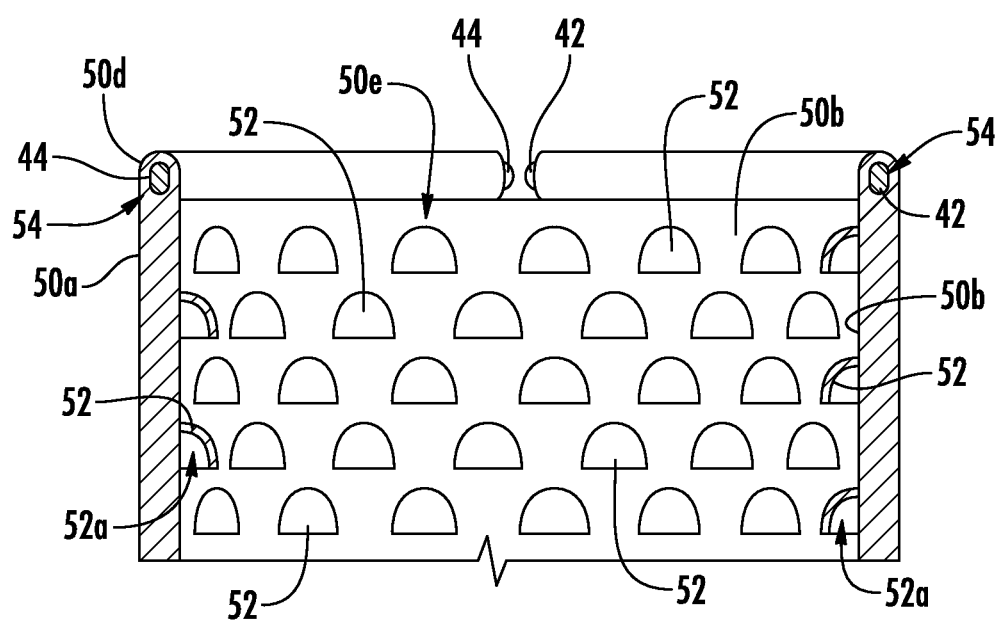
FIG. 4 is an enlarged, cross-sectional view of a portion of a collection bag of the specimen retrieval device of FIG. 1 as taken along section line 4-4 shown in FIG. 2.
Figure 5:
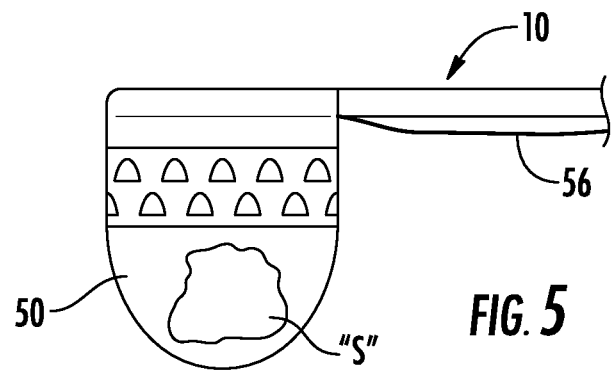
FIGS. 5-8 are progressive views illustrating the specimen retrieval device of FIG. 1 collecting a specimen in the collection bag of the specimen retrieval device.

As seen in FIGS. 2-4, collection bag 50 defines a central bag axis "A" that extends transverse to longitudinal axis "L" of specimen retrieval device 10 when collection bag 50 is coupled to end effector 40 of specimen retrieval device 10. Collection bag 50 includes an outer surface 50a and an inner surface 50b. Collection bag 50 further includes a bottom end portion 50c that is closed and a top end portion 50d that is open. In particular, top end portion 50d of collection bag 50 defines an opening 50e configured to receive a specimen therethrough so that the specimen can be supported in the bottom end portion 50c of collection bag 50. Collection bag 50 further includes a plurality of inverted pouches 52 that extend from inner surface 50b. Inverted pouches 52 are arrayed around a circumference of inner surface 50b of collection bag 50 and can have any suitable shape or configuration. In some embodiments, inverted pouches 52 may be arcuate. Inverted pouches 52 can be provided in a plurality of rows "R" of inverted pouches 52, which may be vertically and/or horizontally spaced apart. Each inverted pouch 52 defines a pocket 52a that is configured to capture fluid such as blood, saline, etc., and/or debris such as small specimen particles like bodily tissue, that move upwardly along inner surface 50b of collection bag 50 when collection bag 50 supports a specimen therein. Inverted pouches 52 are configured to prevent such fluid and/or specimen particles from migrating out of opening 50e of collection bag 50.

Collection bag 50 defines arm channels 54 for selectively mounting collection bag 50 on first and second arms 42, 44 of end effector 40. Collection bag 50 further includes a pull string assembly 56 that is selectively actuatable to close opening 50e of collection bag 50.

Figure 6:
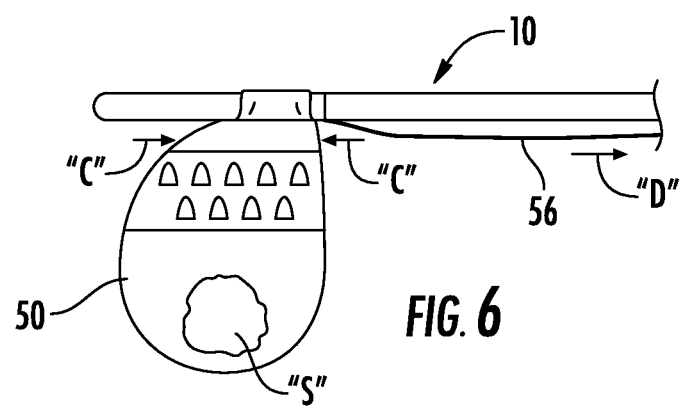
Figure 7:
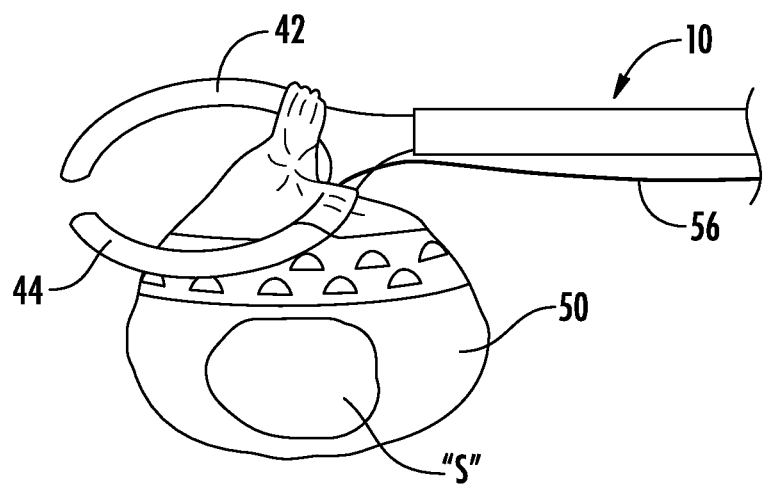
Figure 8:
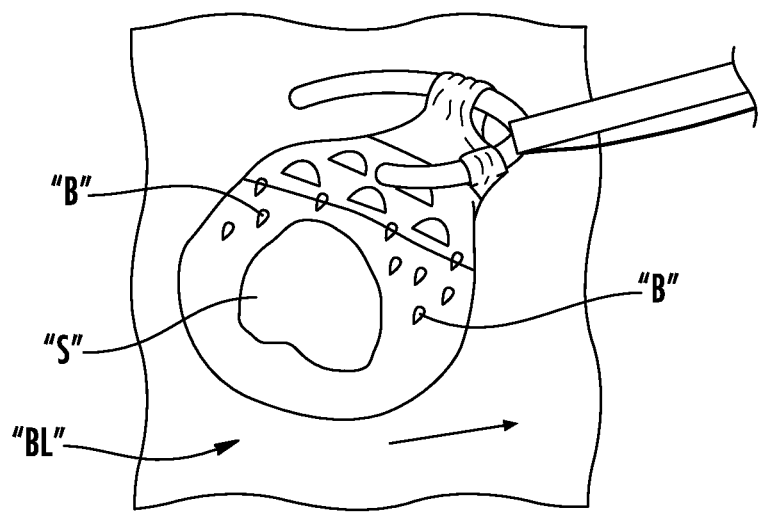
Figure 9:
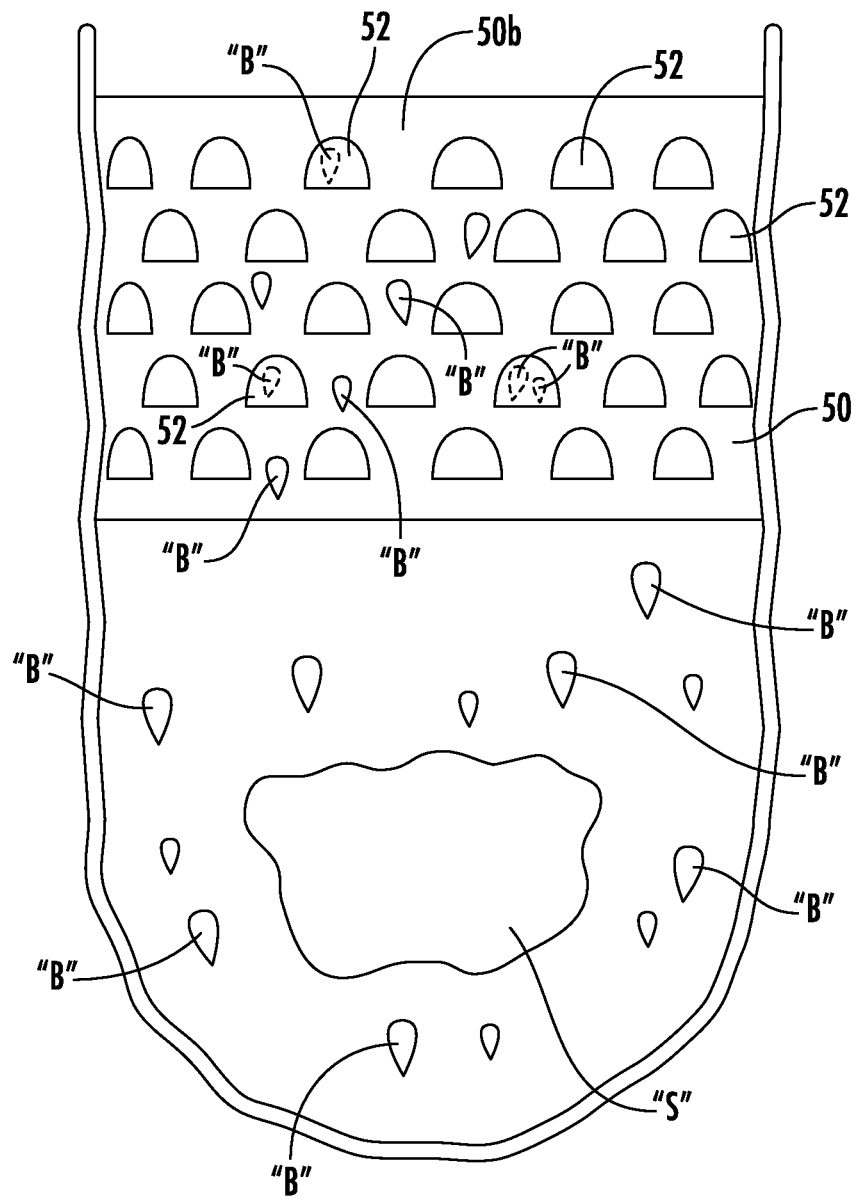
FIG. 9 is an enlarged, side view of a portion of the collection bag supporting the specimen in the collection bag with fluid, such as blood, moving along walls of the collection bag.

As seen in FIGS. 5-9, once specimen "S" is collected in collection bag 50 of specimen retrieval device 10, pull string assembly 56 is drawn proximally, as indicated by arrow "D" (FIG. 6), to cinch opening 50e, from an open position to a closed position, as indicated by arrows "C" illustrated in FIGS. 6 and 7. In particular, as collection bag 50 is cinched closed by pull string assembly 56, a diameter of opening 50e reduced until collection bag 50 is closed or substantially closed to retain pull string assembly 56. Any splatter of fluid or debris, such as blood "B," that migrates along inner surface 50b of collection bag 50, for instance during placement of specimen "S" in collection bag 50 and/or retraction of collection bag 50 out of a body cavity "BC," is captured by inverted pouches 52 to prevent such fluid or debris from leaking through top portion 50d of collection bag 50. Collection bag 50 can be slid off end effector 40 of specimen retrieval device 10 to, for example, test and/or dispose of the specimen "S."

In some embodiments, one or more rows "R" of inverted pouches 52, or portions thereof, may be in and/or out of phase with one another. In various embodiments, at least one row "R" of inverted pouches 52 may include one or more portions that are in and/or out of phase with one or more other portions of the at least one row "R." In some embodiments, inverted pouches 52 may be arranged at random locations about inner surface 50b of collection bag 50.

Although pouches 52 are described herein as inverted, in some embodiments, one or more of pouches 52 may define pockets that open toward any suitable direction including toward the top end portion, laterally, etc., or combinations thereof. In various embodiments, one or more of pouches 52, and/or rows "R" thereof, can be angled at any suitable angle (e.g., in any of the 360 degrees about an axis orthogonal to central bag axis "A.") Further, although shown herein as having single pockets 52a, in certain embodiments, pouches 52 may include any number of pockets 52a (e.g., two, three, etc.) and/or any number of openings into those one or more pockets 52a.

As can be appreciated, collection bag 50 may be made at least partially of any suitable polymeric material such as nylon. In some embodiments, collection bag 50 may be transparent or translucent.

Securement of any of the components of the disclosed devices may be effectuated using known securement techniques such welding, crimping, gluing, heat-shrinking, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that this disclosure is not limited to the precise embodiments described, and that various other changes and modifications may be effected by one skilled in the art without departing from the scope or spirit of this disclosure. Additionally, the elements and features shown or described in connection with certain embodiments may be combined with the elements and features of certain other embodiments without departing from the scope of this disclosure, and that such modifications and variations are also included within the scope of this disclosure. Accordingly, the subject matter of this disclosure is not limited by what has been particularly shown and described.

What is claimed is:

1. A specimen retrieval device, comprising:
   an elongated shaft; and
   an end effector supported on the elongated shaft, the end effector supporting a collection bag, the collection bag including an inner surface and an outer surface, the inner surface of the collection bag including a plurality of pouches, the pouches defining a pocket configured to prevent fluid from migrating out of the collection bag, and the pouches being inverted so that the pockets thereof open toward a bottom of the collection bag.

2. The specimen retrieval device of claim 1, wherein the pouches have an arcuate configuration.

3. The specimen retrieval device of claim 1, wherein the pouches are arranged in a plurality of rows.

4. The specimen retrieval device of claim 3, wherein at least some of the plurality of rows are arranged such that pouches in adjacent rows are offset from one another.

5. The specimen retrieval device of claim 1, wherein each pouch of the plurality of pouches is offset from adjacent pouches of the plurality of pouches.

6. The specimen retrieval device of claim 1, further a pull string assembly that is actuatable to close the collection bag.

7. The specimen retrieval device of claim 1, wherein the collection bag is made at least partially of a polymeric material.

8. The specimen retrieval device of claim 1, wherein the collection bag is transparent.

9. A collection bag for a specimen retrieval device, the collection bag comprising:
- an outer surface;
- an inner surface;
- a bottom end portion; and
- a top end portion including a plurality of pouches extending from the inner surface, wherein the pouches are arranged in a plurality of rows, and at least some of the plurality of rows are arranged such that pouches in adjacent rows are offset from one another.

10. The collection bag of claim 9, wherein the pouches define a pocket configured to prevent fluid from migrating out of an opening defined in the top end portion.

11. The collection bag of claim 10, wherein the pouches have an arcuate configuration.

12. The collection bag of claim 10, wherein the pouches are inverted so that the pockets thereof open toward the bottom end portion.

13. The collection bag of claim 9, wherein each pouch of the plurality of pouches is offset from adjacent pouches of the plurality of pouches.

14. The collection bag of claim 9, wherein the collection bag is made at least partially of a polymeric material.

15. The collection bag of claim 14, wherein the collection bag is transparent.

16. A collection bag for retrieving a tissue specimen, the collection bag comprising:
- a closed bottom end portion;
- an open top end portion that is selectively closable;
- an outer surface; and
- an inner surface including a plurality of inverted pouches that open towards the closed bottom end portion.

\* \* \* \* \*